United States Patent [19]

Moore, Jr.

[11] 3,992,369

[45] Nov. 16, 1976

[54] 2-[(1-CYANO-1-METHYLETHYL)AZO]-2-METHYLPROPIONAMIDE

[75] Inventor: Earl Phillip Moore, Jr., Hockessin, Del.

[73] Assignee: E. I. Du Pont de Nemours and Company, Wilmington, Del.

[22] Filed: Sept. 18, 1975

[21] Appl. No.: 614,685

Related U.S. Application Data

[63] Continuation-in-part of Ser. No. 357,524, May 7, 1973, abandoned.

[52] U.S. Cl. .............................. 260/192; 260/93.7; 260/193; 526/215; 526/217; 526/218; 526/297; 526/303; 526/341; 526/332; 526/348; 526/328; 526/336

[51] Int. Cl.² .............. C07C 107/02; C08F 116/02; C08F 116/12; C08F 120/00

[58] Field of Search ............................. 360/192, 193

[56] References Cited

UNITED STATES PATENTS

| | | | |
|---|---|---|---|
| 2,471,959 | 5/1949 | Hunt | 260/89.5 |
| 2,877,102 | 3/1959 | Levesque | 44/57 |
| 3,282,912 | 11/1966 | Benzing | 260/158 |
| 3,390,146 | 6/1968 | Nield et al. | 260/192 |
| 3,629,227 | 12/1971 | Meckel et al. | 260/174 |
| 3,642,751 | 2/1972 | Logemann et al. | 260/89.5 |

*Primary Examiner*—Floyd D. Higel

[57] ABSTRACT

A new compound, 2-[(1-cyano-1-methylethyl)azo]-2-methylpropionamide, has been found which is useful as an initiator in the polymerization of ethylenically unsaturated compounds.

1 Claim, No Drawings

2-[(1-CYANO-1-METHYLETHYL)AZO]-2-METHYLPROPIONAMIDE

CROSS REFERENCE TO RELATED APPLICATION

This is a continuation-in-part of copending application Ser. No. 357,524, filed May 7, 1973 and now abandoned.

BACKGROUND OF THE INVENTION

Organic and inorganic peroxygen compounds, such as peroxides, hydroperoxides, peresters, persulfates, hydrogen peroxide, etc. are widely employed as free-radical initiators in polymerizations of ethylenically unsaturated compounds. However, peroxygen initiators have shortcomings which limit their usefulness. They often oxidize polymers or leave oxygenated residues which cause discoloration on aging and exposure to light or they alter the color of dyestuffs. Many are shock sensitive and unpredictable in behavior and can cause undesirable chain-branching.

On the other hand, azo initiators such as the azonitriles disclosed in U.S. Pat. No. 2,471,959 and compounds derived from them do not have the undesirable characteristics ascribed to peroxides and are highly useful in vinyl polymerizations. Azo initiators which are water soluble are particularly useful in aqueous solution and emulsion polymerization. However, most water soluble azo compounds have salt-like functional groups (see, for example, U.S. Pat. No. 2,520,338 and U.S. Pat. No. 2,599,300) which introduce functional groups into polymers which can reduce thermal stability as well as detract from physical electrical and mechanical properties. Water insoluble azo compounds such as azodinitriles are known to possess free-radical initiation properties in some aqueous emulsion polymerization systems but are difficult to introduce into aqueous polymerization systems where organic solvents cannot be tolerated. Such azodinitriles decompose to form toxic byproducts. Water soluble azo compounds such as azodiamides are known to possess free-radical initiation properties at high temperatures where most polymerizations are carried out. However, at lower temperatures where the best polymers are made, the azodiamides are not effective. Additionally, the azodiamides decompose to form toxic byproducts. A initiator that is water soluble, effective at lower polymerization temperatures and which possess more favorable toxicity properties is desirable.

SUMMARY OF THE INVENTION

Now in accordance with the invention, a new compound has been discovered, 2-[(1-cyano-1-methylethyl)azo]-2-methylpropionamide, of the structure

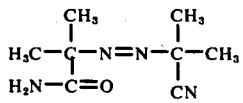

When employed in catalytic quantities, that is, any quantity effective to initiate the polymerization reaction, the unique compound of this invention functions as an excellent catalyst for the polymerization of ethylenically unsaturated compounds. Indeed, as little as 0.01% by weight based on the weight of the monomers easily and effectively initiates the polymerization of any desired ethylenically unsaturated monomers. Generally from about 0.01 to about 2% by weight based upon the weight of the monomers of the compound of the present invenion is employed, preferably 0.05 to 0.5% by weight.

The unique compound of this invention is new, effective, water soluble, neutral, easy to prepare from readily available starting materials and, unlike azo compounds of closely related structure, does not give highly toxic byproducts on decomposition. Polymerizations in aqueous solutions or in emulsions can be carried out effectively with the new azo compound of the present invention.

DETAILED DESCRIPTION OF THE INVENTION

The unique azomonoamide compound of this invention is readily prepared by the hydrogen peroxide-promoted basic hydrolysis of 2,2'-azobis(isobutyronitrile) which is readily available under the tradename "Vazo" 64 (from E. I. du Pont de Nemours and Co.) The 2,2'-azobis(isobutyronitrile) is reacted in solution at a maximum concentration of about 20% by weight of the nitrile, preferably from 8 to 12% at temperatures of from about 25° to about 50° C with hydrogen peroxide in the presence of a base to yield 2-[(1-cyano-1-methylethyl)azo]-2-methylpropionamide. Because the starting compound is insoluble in water, the reaction is generally carried out in an alcohol or acetone solution or in a mixture of from about 2:1 alcohol or acetone to water up to 100% of acetone or alcohol and preferably 100% alcohol is employed. Any suitable water miscible alcohol may be employed in the preparation such as, for example, methanol, ethanol, n-propanol, isopropanol, tert-butyl alcohol and the like but preferably methanol is used.

Any suitable base may be used to prepare the azomonomide of this invention. Representative examples of such bases include ammonium hydroxide and any alkali metal hydroxide such as sodium, potassium and lithium hyroxide. The amount of 100% base which is used on a molar basis ranges from about 0.1 mol per mol of the dinitrile to 1 mol per mol of dinitrile. Concentrations greater than 1 mol per mol of dinitrile may be used if desired. Preferably, however, from about 0.3 to about 0.7 mol of base per mol of the dinitrile is employed. Since the rate of the reaction depends on the concentration of the base one can choose any desired concentration of base which will give the desired speed of reaction. It should be noted, however, that a low yield of the monoamide could be obtained if a very strongly basic solution is used.

The amount of 100% hydrogen peroxide which is used on a molar basis varies from about 1.0 to about 2.5 mols per mol of the dinitrile, preferably 1.75 to 2.20 mols per mol of dinitrile. While less than 1 mol of hydrogen peroxide per mol of the dinitrile can be used, the product thus achieved would contain quantities of unreacted dinitrile, the amounts of which would depend on the degree of the deficiency in the amount of the peroxide employed. On the other hand, more than 2.5 mols of hydrogen peroxide per mol of the dinitrile can be used but increasing amounts of the peroxide would result in increasing amounts of undesired diamide in the reaction product.

The hydrogen peroxide to be used should generally be an aqueous solution containing a minimum of about 3% by weight of hydrogen peroxide. Concentrations of 50% by weight and even higher may be employed although it is preferred to use solutions containing from about 30% to about 50% by weight.

In carrying out the preparation of the azomonoamide, a solution of the dinitrile is prepared and the base is added, generally with rapid stirring. The hydrogen peroxide is then introduced and the reaction is allowed to continue until the evolution of oxygen ceases. Preferential conversion of only one of the cyano groups to the amide group occurs to give the monoamide in favorable proportion to the completely reacted diamide. The resulting azomonoamide is recovered as a precipitate from the reaction mixture and has a half life in solution at 80° C of about 10 hours.

If desired, the azomonoamide can be purified by any suitable method. Preferably, the final mixture is treated with methylene chloride to dissolve the monoamide and the dinitrile while the diamide remains undissolved. The methylene chloride is then evaporated from the mixture of the dinitrile and the azomonoamide, which mixture is then stirred into warm or hot water, preferably about 10 grams of mixture per 100 grams of water at a temperature of 60° C is used. The dinitrile, which is insoluble in water is then filtered off and the water is cooled to 0° C to crystallize out the monoamide.

The azomonoamide of this invention has a combination of unique properties which make it extremely useful as a free-radical initiator for the polymerization of many unsaturated organic compounds commonly referred to as monomers. Further, the unique properties of the azomonoamide of the present invention are surprising and unexpected over structurally related azo compounds, such as the azodinitrile, 2,2'-azobis(isobutronitrile) from which it is prepared and the azodiamide, 2,2'-azobis(isobutyramide) which is formed if the reaction of the dinitrile and hydrogen peroxide is carried further than required to produce the azomonoamide. The azomonoamide of this invention is water soluble and gives a neutral solution in water and does not have salt-like character, all of which are highly important in the preparation of polymers in aqueous solution or as emulsions since the azomonoamide will not interfere with or offset the properties of critical agents which go into the various polymerization recipes, nor will it introduce functional groups into polymers which can hurt properties.

The azodiamide, though water soluble, is a poor free-radical initiator at temperatures below 60° C where many polymerizations are most favorably conducted. The diamide exhibits the peculiar behavior of decomposing fairly rapidly at temperatures of 25° C and above and must be refrigerated, a costly necessity, while the monoamide can be stored indefinitely at 25° C. The azomonomide of the present invention, on the other hand, is quite effective at temperatures below 60° C.

The water soluble character of the azomonoamide gives it utility beyond that of the water insoluble azodinitrile because it is possible to introduce aqueous solutions of the azomonoamide into polymerization reactors. In many instances the use of organic solvents in aqueous polymerizations is undesirable because of polymer contamination or interference with the polymerization process. Water insoluble initiators such as the dinitrile can be introduced into aqueous polymerization systems only with difficulty. Emulsions or dispersions in water can be prepared but many times the solids particles, no matter how fine, erode and plug pumps, injection nozzles, small orifice equipment, etc.

Toxicity of byproducts of the initiator upon decomposition, that is, products which are formed from that fraction of the initiator which does not cause polymerization, is an important factor in selecting a useful initiator. Many aqueous polymer solutions as well as aqueous polymer emulsions go into commercial products (for example, paints) which dry down at ambient temperature and are not heated thereafter. Toxic impurities in many such products cannot be eliminated and could present a health hazard to users of these products. The decomposition byproducts from the dinitrile and the diamide are highly toxic while the byproduct from the monoamide is appreciably less toxic.

The unique compound of this invention is an excellent initiator for the polymerization of any desired ethylenically unsaturated compounds such as the polymerizable vinyl and vinylidene compounds including, vinyl monomers, for example, butadiene, isoprene, the methyl, ethyl, butyl and hexyl ester of acrylic, methacrylic and cyanoacrylic acids, acrylonitrile, methacrylonitrile, acrylamide and methacrylamide, vinyl acetate and propionate, vinyl chloride, vinylidene chloride, methyl vinyl ether and any of the ethylenically unsaturated monomers listed in U.S. Pat. No. 3,225,119 issued to William P. Baker, Jr. on Dec. 21, 1965.

Since the unique initiator of this invention is water soluble, the polymerization of the ethylenically unsaturated compound may be carried out in an aqueous solution as well as in a dispersion or emulsion.

Any suitable reaction conditions may be observed in carrying out the polymerization of the ethylenically unsaturated monomers using the unique initiator of this invention. For example, temperatures as low as 25° C and as high as 160° C may be employed in carrying out the polymerization, preferably 50° to about 100° C. The optimum temperature for a particular monomer will depend upon its desired reactivity. The polymerization may be carried out at atmospheric pressure, under a vacuum or at pressures above atmospheric pressure. In some instances an inert atmosphere such as nitrogen, argon and the like may be used to advantage.

The invention is further illustrated but is not intended to be limited by the following examples in which all parts and percentages are by weight unless otherwise specified.

EXAMPLE 1

Twenty-five parts of α,α'-azobis(isobutyronitrile) (0.152 mol) are dissolved in 225 parts of absolute methanol and 8.5 parts of a 50% solution of sodium hydroxide in water are added with stirring. To the rapidly stirred solution are added 22.5 parts of a 50% solution of hydrogen peroxide in water (0.33 mol) in about 5 minutes. Oxygen is evolved during the reaction and the temperature increases to 45° C. A clear yellow solution is obtained. The reaction is essentially complete about 5 minutes after the hydrogen peroxide addition is complete, at which point the evolution of oxygen ceases. Stirring is continued for 15 minutes longer. Liquid is removed by blowing air across the surface of the reaction mixture until no more precipitation of solid occurs. The air dried solid is extracted with methylene chloride to dissolve unreacted α,α'-azobis-(isobutyronitrile) and the monoamide 2-[(1-cyano-1-methylethyl)-azo]-2-methylpropionamide, leaving α,α'-azobis(isobutyramide). The methylene chloride is evaporated and the residue is treated with warm water (50° C) to dissolve the monoamide, leaving the insoluble dinitrile behind as a precipitate. The solution is cooled to 0° C to precipitate the monoamide. A 50% yield of monoamide is obtained, 13.7 g.

Elemental analysis of the product gave an average of carbon, hydrogen and nitrogen of 52.75, 7.80 and 30.55, respectively, against theoretical values of 52.8, 7.7 and 30.8, respectively, for the empirical formula $C_8H_{14}N_4O$. A molecular weight determination in dioxane yielded 180 against a theoretical 182. The monoamide structure was verified by nuclear magnetic resonance and infrared spectra studies. The half life of the product in water at 80° C was determined as 11.2 hours via measurement of the decrease in UV absorption with time.

EXAMPLE 2

The preparation of Example 1 is repeated except that 25 parts of the hydrogen peroxide are employed. As a result, 16.4 g or a 60% yield of monoamide is obtained.

The half life of the product in dimethylformamide at 80° C was measured using ultraviolet absorption: $t_{1/2} = \ln 2/k = 11.2$ hours.

EXAMPLE 3

A mixture of 100 parts of distilled water, 1 part of ammonium lauryl sulfate and 50 parts of vinyl acetate was prepared and purged with nitrogen in a 500 ml flask contaning a stirrer, a nitrogen inlet and a condenser. The flask was immersed in a steam bath. About 2.5 ml of a 1.8% aqueous solution (0.045 g) of the product of Example 2 were added. The temperature of the reaction mixture was raised quickly to between 70° and 80° C and stirred. After about 20 minutes the reaction mixture becomes cloudy. The reaction appears to be complete in about 1 hour but the reaction mixture is mantaned at about 75° C with stirring for a further 30 minutes. An opalescent blue emulsion is obtained which is vacuum treated to remove any trace of monomer. The emulsion is coagulated in a salt solution and the polymer is removed by filtration, washed with water and air dried. A yield of 85% of polyvinyl acetate having an inherent viscosity of 1.2 as determined in a chloroform solution (0.5%, 30° C) is obtained.

EXAMPLE 4

The apparatus of Example 3 is flushed with nitrogen, 120 ml of water are introduced to the flask and the system is purged with nitrogen. About 0.1 part of the azoamide of Example 2 is dissolved in the water after which 2 parts of sodium lauryl sulfate and 80 parts of acrylonitrile are added. The system is again purged with nitrogen and the reaction mixture is heated to from about 65° to about 70° C. The mixture becomes milky after only a few minutes. Polymerization is allowed to proceed for 4 hours at 65° to 70° C and a stable milky dispersion is obtained. The emulsion is coagulated in a salt solution and the polymer is removed by filtration, washed with water and air dried. A yield of 90% of polyacrylonitrile having an inherent viscosity of 8.5 as determined in dimethylformamide solution (0.5%, 30° C) is obtained.

EXAMPLE 5

Three closely structurally related azo compounds were evaluated in the emulsion polymerization of styrene:

A. 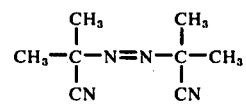

2,2'-azobis(isobutyronitrile)

B. 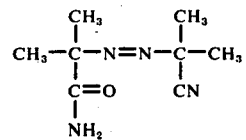

2-[(1-cyano-1-methylethyl)azo]-2-methyl-propionamide

C. 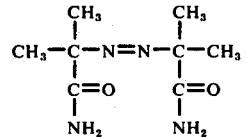

2,2'-azobis(isobutyramide).

In a heavy-walled 300 ml glass resin kettle equipped with thermometer, stirrer and gas inlet port, was introduced 50 g freshly distilled styrene, 100 g distilled water, 0.1 g azo initiator and 1.0 g sodium lauryl sulfate. Nitrogen was bubbled through the mixture to displace air and disperse the styrene. The vessel was then placed in a thermostated water bath at 58° C and the mixture was stirred for 5 hours.

After the reaction period, the contents of the kettle was poured into 500 ml acetone to precipitate any polymer. The polymer then was washed with acetone, dried and weighed. The azo initiator designated A above gave 41.6 g polymer. The azo initiator B gave 40.5 g polymer. The azo initiator C gave no polymer.

Samples of the byproducts of thermal decomposition of azo initiators A, B and C were determined to have the following ALD values:
A. 60.0 mg/Kg
B. 300 mg/Kg
C. 90.0 mg/Kg The byproducts of azo compound B with the ALD value of 300 mg/Kg is appreciably less toxic than either the dinitrile A or the diamide C.

ALD is Approximate Lethal Dose and is known in the art. The thermal decomposition products of initiators A, B and C were administered orally to a young adult ChR-CD male rat in single doses. The ALD is the amount in milligrams of compound required to kill the rat in a single dose per kilogram of body weight of rat. The ALD value of nicotine is 50 mg/Kg and of HCN is 4 mg/Kg.

Although the invention has been described in considerable detail in the foregoing, it is to be understood that such detail is solely for the purposes of illustration and that variations may be by one skilled in the art without departing from the spirit and scope of the invention.

What is claimed is:
1. The compound

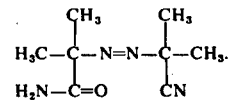

* * * * *